United States Patent [19]

Fischer et al.

[11] Patent Number: 4,550,083
[45] Date of Patent: Oct. 29, 1985

[54] KARL-FISCHER REAGENT AND PROCEDURE FOR THE DETERMINATION OF WATER USING IT

[75] Inventors: Wolfgang Fischer; Georg Seitz, both of Darmstadt; Karl-Dieter Krenn, Pfungstadt, all of Fed. Rep. of Germany

[73] Assignee: Merck Patent Gesellschaft mit beschränkter Haftung, Darmstadt, Fed. Rep. of Germany

[21] Appl. No.: 466,187

[22] Filed: Feb. 14, 1983

[30] Foreign Application Priority Data

Feb. 12, 1982 [DE] Fed. Rep. of Germany ....... 3204962

[51] Int. Cl.$^4$ ............................................. G01N 33/18
[52] U.S. Cl. ..................................... 436/42; 204/1 T
[58] Field of Search .................... 436/39, 42; 204/1 T

[56] References Cited

U.S. PATENT DOCUMENTS

| 2,967,155 | 1/1961 | Blomgren et al. | |
| 4,295,990 | 10/1981 | Verbeek et al. | |
| 4,351,744 | 9/1982 | Muroi et al. | 436/42 |
| 4,355,998 | 10/1982 | Verbeek et al. | 436/39 |
| 4,378,972 | 4/1983 | Scholz | 436/42 |
| 4,385,124 | 5/1983 | Verbeek et al. | 436/42 |
| 4,416,997 | 11/1983 | Fischer et al. | 436/42 |
| 4,429,048 | 1/1984 | Scholz | 436/42 |

FOREIGN PATENT DOCUMENTS

| 35066 | 9/1981 | European Pat. Off. |
| 728947 | 4/1955 | United Kingdom |

OTHER PUBLICATIONS

Smith et al., J.A.C.S. 61, 2407, (1939).
Johansson, Anal. Chem. 28, 1166, (1956).
Verhoef et al., Anal. Chem. Acta 94, 395, (1977).

*Primary Examiner*—Arnold Turk
*Attorney, Agent, or Firm*—Millen & White, P.C.

[57] ABSTRACT

A Karl Fischer reagent useful in the determination of water, comprises sulfur dioxide, iodine and a salt which is a system compatible addition compound of a nitrogen-containing organic base having a $pK_b < 10$ with a weak aromatic carboxylic acid having a $pK_a > 2$.

17 Claims, No Drawings

KARL-FISCHER REAGENT AND PROCEDURE FOR THE DETERMINATION OF WATER USING IT

BACKGROUND OF THE INVENTION

The present invention relates to a modified Karl-Fischer reagent useful in the determination of water. It contains a salt, sulfur dioxide and iodine. It also relates to a procedure for the determination of water using this reagent.

A number of proposals are known from the literature for replacing pyridine in the Karl-Fischer reagent by other substances. In Anal. Chim. Acta 94, 395 (1977), sodium acetate is used as a substitute for pyridine. However, this substitution involves certain disadvantages. The acetate is formed, for example, with the alcohol used as solvent. Water is liberated. This obviously interferes with a method of determination of water. For this reason, the solutions are not stable and their blank value increases continuously.

In British Pat. No. 728,947, alcoholates, phenolates and metal salts of weak organic acids are mentioned in addition to acetates as substitutes for pyridine. A recheck of the substances mentioned in the patent specification showed that these are not suitable as substitutes for pyridine, in some cases because of inadequate solubility and in some cases because of insufficient stability of the corresponding ready to use solutions. Furthermore, it is known that on replacing pyridine by amines, stable end products cannot be obtained upon titration (Anal. Chem. 28, 1166 (1956)). DOS 30 48 237 (U.S. Ser. No. 333,100 of Dec. 21, 1981) discloses a modified Karl-Fischer reagent wherein pyridine is replaced by ammonia or an alkali or alkaline earth metal benzoate.

In order to avoid these disadvantages, attempts have very recently been made to replace pyridine by aliphatic amines at a particular molar ratio to sulfur dioxide (German Offenlegungsschrift 3,010,436 corresponding to U.S. application Ser. No. 245,405 of Mar. 19, 1981) or by heterocyclic compounds (European Pat. No. 35,066). However, these pyridine substitutes again do not provide the desired results, since the stability of the end point varies with the amount of water to be titrated.

SUMMARY OF THE INVENTION

Accordingly, it is an object of this invention to provide a modified Karl-Fischer reagent, which is stable, enables exact analytical results and shows the most stable end point possible, even for variable amounts of water.

Upon further study of the specification and appended claims, further objects and advantages of this invention will become apparent to those skilled in the art.

These objects have been attained, surprisingly, in that a Karl-Fischer reagent of this type is provided when in the conventional Karl-Fischer reagent, instead of pyridine, a salt of a nitrogen-containing compound with a weak organic acid, preferably an aromatic carboxylic acid, is used. These substances are very readily soluble in the reagent solution, virtually do not react at all with alcohols to form esters, are very stable upon storage and provide stable end points even on titration over a wide range of water contents.

Additional use of acids in the Karl-Fischer reagent is in fact also mentioned in European Pat. No. 35,066; however, the mentioned acids do not provide salts utilizable for the reagent according to this invention (using e.g., sulfuric acid or hydriodic acid) or the resultant reagent is destabilized by addition of the acid (using e.g., formic acid, oxalic acid or acetic acid).

The present invention hence relates to a Karl-Fischer reagent useful in the determination of water, comprising a salt, sulfur dioxide and iodine, wherein the salt is present as a compound of an organic base with a weak organic acid. Salts of a nitrogen-containing compound having a basicity constant $pK_b < 10$ with an aromatic carboxylic acid having a $pK_{diss}(pK_a) > 2$, are preferred. The pK values refer to the initial dissociation.

The invention further relates to a procedure for the determination of water using the Karl-Fischer reagent of this invention.

DETAILED DISCUSSION

The Karl-Fischer reagent of this invention comprises either two solutions, a dissolving agent and a titrating agent, or a so-called all-in-one solution which contains all the constituents in a single solution. The dissolving agent contains sulfur dioxide and the salt in a solvent and serves to take up the sample to be investigated for its water content. The titrating agent is a solution of iodine in a solvent, which solution has been adjusted to a constant titer. However, the dissolving agent and the titrating agent can also be formed as an all-in-one solution, as already mentioned. This is sufficiently stable to be employed in a customary manner as a titration liquid. The all-in-one solution is advantageous particularly when the substance to be investigated is more soluble in another solvent than in the solvent contained in the dissolving agent. In this case, the rate of reaction is also independent of the rate of dissolution.

Organic bases suitable for forming salts according to this invention are preferably primary, secondary or tertiary aliphatic or alicyclic amines, usually derived from hydrocarbons, e.g., ethanolamine, diethanolamine, triethanolamine, diethylamine, triethylamine, diisopropylamine, tri-n-butylamine, ethylenediamine, morpholine, N-methylmorpholine and the like or heterocycles (e.g., of up to 5-15 ring atoms in total) having at least one ring nitrogen atom (e.g., 1-3 such N-atoms), the remainder usually being C-atoms or including up to 3 ring O-atoms, e.g., imidazole ($pK_b=7$), pyridine ($pK_b=8.8$), quinoline ($pK_b=9$) or the like.

Examples of suitable weak acids include aromatic carboxylic acids, such as benzoic acid and its 2-mono-$C_{1-6}$-alkyl or 2,6-di-$C_{1-6}$-alkyl derivatives.

Diethanolammonium benzoate, triethanolammonium benzoate and imidazolium benzoate are particularly preferred for use in the reagent of this invention.

The molar ratio of salt to sulfur dioxide is usually in the range of from 10:1 to 1:1, preferably of 3:1 to 1:1. The amount of iodine is conventionally determined, e.g., in dependence on the estimated amount of water in the sample.

Suitable solvents, both for the dissolving and the titrating agent, include all solvents described in the literature for this purpose, preferably alcohols and/or glycols, in particular lower alcohols, such as methanol, ethanol, propanol and the like and ethylene glycol and ethylene glycol mono(lower)alkyl ethers. The solvents can be used alone or in any desired mixing ratio. Thus, for example, it is possible to dissolve the salt of this invention in an alcohol or in a glycol or in any desired mixing ratio of alcohols, glycols or mixtures of the two types of solvents, to then add the requisite amount of sulfur dioxide and, in the case of the so-called all-in-one solution, also to add iodine.

A number of advantages result from the use of the salts of this invention: the changeover at the equivalence point is clearer and more stable than with the customary Karl-Fischer reagents; the reagent is more soluble and thus can be used more widely, and overall it is environmentally acceptable and reasonably priced.

Using the Karl-Fischer reagent according to this invention, the end point of the titrimetric water determination can be determined visually, photometrically or electrometrically (dead-stop method or coulometric method). The reagent is suitable both for use in automatic titrators and also as a field method, the field method being made possible for the very first time by replacing the customary methanol by any of the mentioned low vapor pressure solvents.

In general, the titration takes place with exclusion of atmospheric moisture. Nowadays, electrometric titration, in particular the so-called dead-stop method, is preferred. This procedure depends on a deliberately produced polarization at two identical platinum electrodes. On applying a small potential difference, the voltage produced by the polarization is compensated and the flow of current is interrupted. The end point of the titration is indicated by a large deflection of the galvanometer with subsequent complete immobility, which is due to the sharp transition from polarization or depolarization of one electrode to complete depolarization or polarization of both electrodes.

Unless indicated otherwise herein, all details of this invention are fully conventional and disclosed, e.g., in J.A.C.S. 61, 2407 (1939), whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

For the preparation of the dissolving agent and the titrating agent, the particular substances mentioned below were dissolved in the mentioned appropriate solvent:
(a) Dissolving agent
341 g of diethanolammonium benzoate (1.5 M) and 64 g of sulfur dioxide (1 M) in 1 liter of methanol
(b) Titrating agent
50 g of iodine in 1 liter of methanol The substance to be investigated for its water content was dissolved to the customary extent appropriate for the estimated water content in 20 ml of the dissolving agent and titrated to the end point with the titrating agent, with constant stirring and exclusion of atmospheric moisture.

EXAMPLE 2

The following Karl-Fischer solutions were prepared:
(a) Dissolving agent
407 g of triethylammonium benzoate (1.5 M) and 32 g of sulfur dioxide (0.5 M) in 1 liter of ethylene glycol monomethyl ether
(b) Titrating agent
50 g of iodine in 1 liter of ethylene glycol monomethyl ether.

The same results were obtained with these solutions as with the solutions according to Example 1. Furthermore, the results did not change even after partial or complete replacement of the ethylene glycol monomethyl ether by methanol.

EXAMPLE 3

The following Karl-Fischer solutions were prepared:
(a) Dissolving agent
143 g of imidazolium benzoate (0.75 M) and 32 g of sulfur dioxide (0.5 M) in 0.5 liter of ethylene glycol monomethyl ether
(b) 50 g of iodine in 1 liter of methanol.

The same results were obtained with these solutions as with the solutions according to Examples 1 and 2.

EXAMPLE 4

An all-in-one solution was prepared from:
286 g of imidazolium benzoate (1.5 M), 64 g of sulfur dioxide (1 M) and 70 g of iodine in 0.5 liter of ethylene glycol monomethyl ether.

The substance to be investigated for its water content was dissolved in 20 ml of a solvent and titrated with the all-in-one solution. 1 ml of this solution corresponds to about 6 mg of water.

EXAMPLE 5

An all-in-one solution was prepared from:
341 g of diethanolammonium benzoate (1.5 M), 64 g of sulfur dioxide (1 M) and 70 g of iodine in 1 liter of ethylene glycol monomethyl ether.

The substance to be investigated for its water content was dissolved in 20 ml of a solvent and titrated with the all-in-one solution. 1 ml of this solution corresponds to about 3 mg of water.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A Karl-Fischer reagent useful in the determination of water comprising a Karl-Fischer solvent, sulfur dioxide, iodine, and a salt which is a Karl-Fischer reagent compatible addition compound of a nitrogen-containing organic base having a $pK_b < 10$ with a weak aromatic carboxylic acid having a $pK_a > 2$.

2. A Karl-Fischer reagent of claim 1, wherein the organic base is ethanolamine, diethanolamine, triethanolamine, diethylamine, triethylamine, diisopropylamine, tri-n-butylamine, ethylenediamine, morpholine, N-methyl-morpholine, imidazole, pyridine or quinoline.

3. A Karl-Fischer reagent of claim 1, wherein the aromatic carboxylic acid is benzoic acid or 2-monoalkyl or 2,6-dialkyl substituted benzoic acid.

4. A Karl-Fischer reagent of claim 1, wherein the salt is diethanolammonium benzoate, triethanolammonium benzoate or imidazolium benzoate.

5. A Karl-Fischer reagent of claim 1, wherein the solvent is a lower alkanol, a lower alkane glycol or an ethylene glycol monoalkyl ether.

6. A Karl-Fischer reagent of claim 1, wherein the molar ratio of the salt to sulfur dioxide is 10:1 to 1:1.

7. A Karl-Fischer reagent of claim 1, wherein the molar ratio of the salt to sulfur dioxide is 3:1 to 1:1.

8. A Karl-Fischer reagent of claim 1, wherein the solvent is methanol.

9. A Karl-Fischer reagent of claim 1, wherein the solvent is an ethylene glycol monoalkyl ether.

10. In a method for determining water in an unknown sample using a Karl-Fischer reagent, the improvement wherein the Karl-Fischer reagent is that of claim 1.

11. A dissolving agent for use in a Karl-Fischer reagent comprising a Karl-Fischer solvent, sulfur dioxide and a salt which is an addition compound of a nitrogen-containing organic base having a $pK_b < 10$ with a weak aromatic carboxylic acid having a $pK_a > 2$.

12. A Karl-Fischer reagent of claim 11, wherein the solvent is a lower alkanol, a lower alkane glycol or an ethylene glycol monoalkyl ether.

13. A Karl-Fischer reagent of claim 12, wherein the solvent is methanol.

14. A Karl-Fischer reagent system useful in the determination of water comprising a first solution containing a Karl-Fischer solvent, sulfur dioxide and a salt which is an addition compound of a nitrogen-containing organic base having a $pK_b < 10$ with a weak aromatic carboxylic acid having a $pK_a > 2$, and a second solution of iodine in a Karl-Fischer solvent.

15. A Karl-Fischer reagent of claim 11, wherein the solvent is a lower alkanol, a lower alkane glycol or an ethylene glycol monoalkyl ether.

16. A Karl-Fischer reagent of claim 14, wherein the solvent is methanol.

17. In a method for determining water in an unknown sample using a Karl-Fischer reagent, the improvement wherein the Karl-Fischer reagent is that of claim 14.

* * * * *